United States Patent
Domschke et al.

(10) Patent No.: US 7,091,375 B2
(45) Date of Patent: Aug. 15, 2006

(54) METHOD FOR THE PRODUCTION OF 2=-KETO-L-GULONIC ACID $C_4$–$C_{10}$ ALKYL ESTERS

(75) Inventors: Thomas Domschke, Speyer (DE); Martin Merger, Ludwigshafen (DE); Georg Grossmann, Mannheim (DE); Tillmann Faust, Weisenheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 10/534,334

(22) PCT Filed: Nov. 7, 2003

(86) PCT No.: PCT/EP03/12458

§ 371 (c)(1),
(2), (4) Date: Jun. 6, 2005

(87) PCT Pub. No.: WO2004/043880

PCT Pub. Date: May 27, 2004

(65) Prior Publication Data

US 2006/0058550 A1 Mar. 16, 2006

(30) Foreign Application Priority Data

Nov. 11, 2002 (DE) ............... 102 52 659

(51) Int. Cl.
*C07D 305/12* (2006.01)

(52) U.S. Cl. ...................... 560/174; 560/186
(58) Field of Classification Search ........ 560/174, 560/186

See application file for complete search history.

(56) References Cited

U.S. PATENT DOCUMENTS

| | | | |
|---|---|---|---|
| 5,128,487 A | 7/1992 | Tomislav et al. | |
| 5,391,770 A | 2/1995 | Le Fur et al. | |
| 5,744,634 A | 4/1998 | Veits | |
| 6,028,215 A | 2/2000 | Bessling et al. | |
| 6,274,744 B1 | 8/2001 | Burst et al. | |
| 6,573,400 B1 | 6/2003 | Böttcher et al. | |
| 6,617,463 B1 | 9/2003 | Böttcher et al. | |

FOREIGN PATENT DOCUMENTS

| | | |
|---|---|---|
| DE | 198 29 809 | 1/1999 |
| DE | 199 38 980 | 2/2001 |
| DE | 199 54 511 | 5/2001 |
| EP | 0 403 351 | 12/1990 |

(Continued)

*Primary Examiner*—Deborah D. Carr
(74) *Attorney, Agent, or Firm*—Connolly Bove Lodge & Hutz LLP

(57) ABSTRACT

The invention relates to a method for producing 2-keto-L-gulonic acid-$C_4$–$C_{10}$ alkyl ester by esterifying 2-keto-L-gulonic acid (KGS) with an unsaturated, branched or unbranched $C_4$–$C_{10}$ alcohol. The inventive method is characterized by the fact that an aqueous KGS solution is reacted with a $C_4$–$C_{10}$ alcohol up to an esterification degree of 20 to 70 percent in a pre-esterification process carried out under acidic catalysis conditions; and the obtained product is dehydrogenated with an unsaturated, branched or unbranched $C_4$–$C_{10}$ alcohol in a continuous rectification device, whereby the esterification reaction continues, n-butanol preferably being used as the alkyl alcohol. In a preferred embodiment, the aqueous KGS solution is concentrated up to or beyond the limit of solubility prior to the esterification process, preferably by catalyzing a homogeneous or heterogeneous catalyst, especially sulfonic acid, at temperatures of 50 to 120° C. In another embodiment, the produced KGS ester is reacted in one or several additional steps so as to obtain L-ascorbic acid.

15 Claims, 2 Drawing Sheets

FOREIGN PATENT DOCUMENTS

Figure 1:
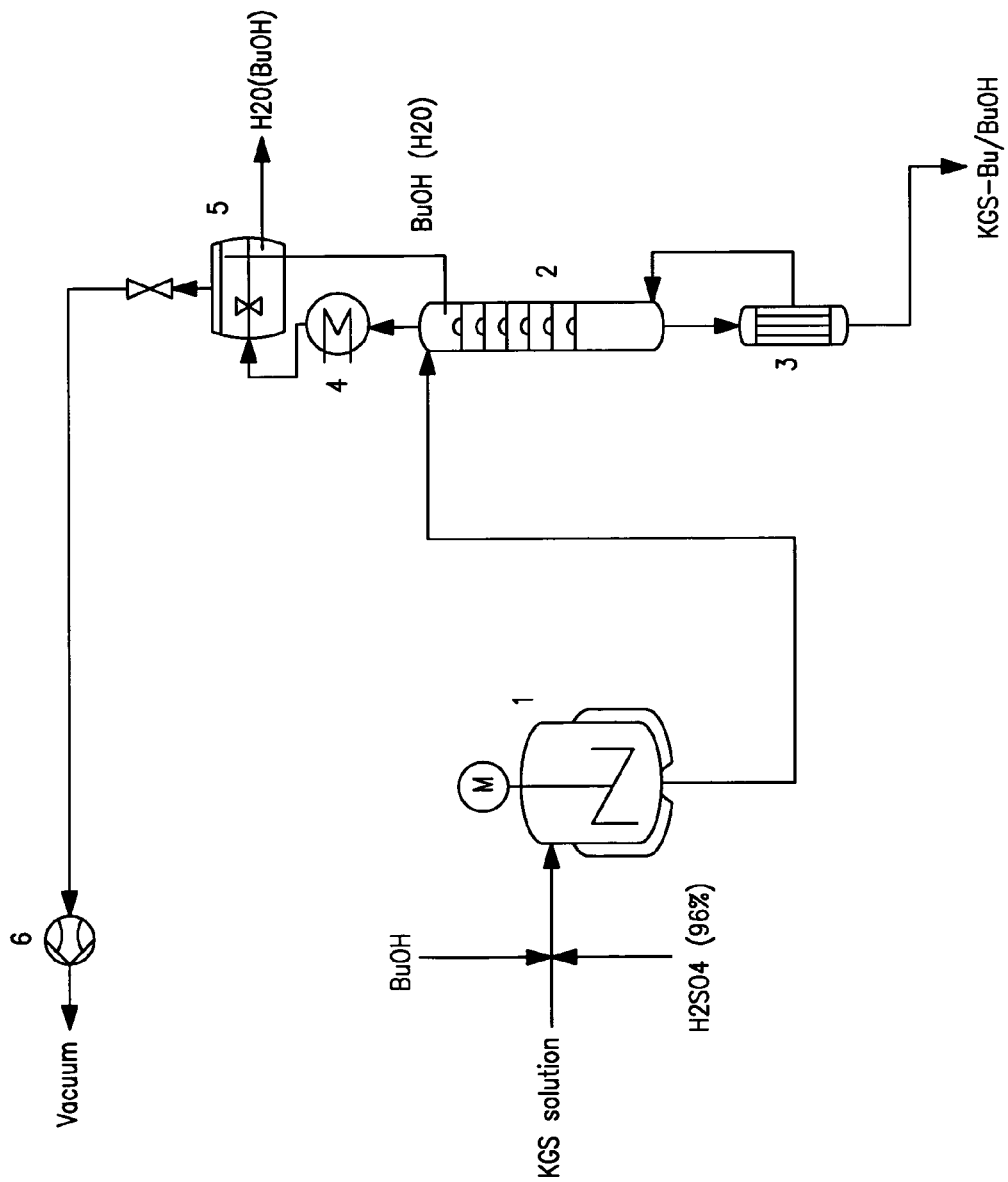

| | | |
|---|---|---|
| EP | 0 403 993 | 12/1990 |
| EP | 0 535 927 | 4/1993 |
| EP | 0 671 405 | 9/1995 |
| WO | WO-97/43433 | 11/1997 |
| WO | WO-99/03853 | 1/1999 |
| WO | WO-01/85711 | 11/2001 | ically practiced processes, the KGA, before esterification, is crystallized or precipitated, dried and calcined in a complex manner. In the subsequent esterification, the water of reaction remains in the mixture, the degree of esterification remains below 100%, as a result of which the overall yield of this process is decreased. The $C_2$- and $C_3$-alcohols exhibit similar material behavior and are therefore scarcely used industrially.

METHOD FOR THE PRODUCTION OF 2=-KETO-L-GULONIC ACID $C_4C_{10}$ ALKYL ESTERS

RELATED APPLICATIONS

This application is a national stage application (under 35 U.S.C. 371) of PCT/EP2003/012458 filed Nov. 7, 2003, which claims benefit to German application 102 52 659.1 filed Nov. 11, 2002.

2-Keto-L-gulonic esters are important intermediates for the synthesis of L-ascorbic acid (vitamin C). The esterification of 2-keto-L-gulonic acid (KGA) with a lower alcohol is known from numerous publications. Generally, a $C_1$–$C_4$-ester of KGA is first prepared, since this is better soluble in organic solvents than KGA and can be converted with high selectivity into ascorbic acid or ascorbate, and preferably methyl and butyl esters are used.

In principle, in this type of reaction, the yield is limited by the esterification equilibrium. The completeness of the respective esterification (degree of esterification) is primarily determined by the residual water content in the reaction mixture, since the esterification reaction is in equilibrium with the reverse reaction (hydrolysis).

In the case of the customary processes, including the Reichstein process, to achieve a high degree of esterification and thus a satisfactory yield, a long boiling time is customarily selected. However, this has an adverse effect on purity, since not only 2-keto-L-gulonic acid but also its methyl ester can form further byproducts under these conditions.

In many known processes, the esterification profits from an alcohol excess or from a continuous removal of the water formed.

Various methods have been proposed to reduce the water content during esterification. Water can be removed during the reaction by continuous distillation of the water/alcohol mixture, treating the distillate with molecular sieves and recycling the alcohol thus dried (Pol. Pat. 57042; Pol. Pat. 57573). Another possible method mentioned has been continuous distillation of the water/alcohol mixture during the reaction and replacement with fresh dry alcohol (EP-A-0 535 927). In both cases, a large amount of alcohol must be distilled off with a correspondingly high energy consumption. Furthermore, reaction times of up to 10 hours are necessary, with the risk of decomposition and side reactions.

EP-A-0 671 405 describes a process for preparing 2-keto-L-gulonic methyl ester or ethyl ester by esterifying 2-keto-L-gulonic acid with methanol or ethanol, respectively, in the presence of an acid ion exchanger.

EP-A-0 403 993 describes a process for preparing 2-keto-L-gulonic methyl ester, in which the esterification is carried out only partially, that is to say not to the extent that the esterification equilibrium has been achieved.

In a process described in WO 99/03853, 2-keto-L-gulonic acid is reacted in a two-stage esterification process to form 2-keto-L-gulonic esters, the solution formed after the first esterification step being at least in part evaporated to remove the water of reaction formed and the resultant residue being subjected to a second esterification process.

WO 97/43433 and U.S. Pat. No. 5,391,770 describe the synthesis of 2-keto-L-gulonic butyl ester by refluxing 2-keto-L-gulonic acid for several hours in butanol in the presence of p-toluenesulfonic acid and subsequently crystallizing out the product of value by cooling the reaction mixture.

DE-A-198 29 809 relates to a process for preparing esters from alcohol and carboxylic acid using a catalyst and removing the ester in a rectification column equipped with internals.

DE 199 38 980 describes a process in which a $C_1$- to $C_{10}$-alkyl ester of KGA is produced by carrying out the esterification reaction in a liquid film on a hot surface with simultaneous removal of water.

Since the boiling temperature of methanol is far below that of water, water can be removed from a water/methanol mixture of the reaction mixture only with a very high energy consumption in a reactive distillation (distillation of an MeOH/water mixture of only a low water content, condensation, dehydration and recirculation of large amounts of methanol). The consequence of this is that, in industri- Higher alcohols, that is to say $C_4$- to $C_{10}$-alkyl alcohols, especially the $C_4$-alcohols, and here in particular 1-butanol, usually form an azeotrope with water. In the case of n-butanol, a heteroazeotrope exists which contains considerable amounts of water (approximately 40% (m/m)). Here, therefore, during the esterification, water can be removed in-situ from the reaction mixture with a relatively low energy consumption by distillation with recirculation of the BuOH phase of the condensed heteroazeotrope. This has two essential advantages:

1. The KGA need neither be calcined nor dried, it can even be introduced into the process as aqueous solution.
2. The esterification can be carried out virtually to completion, since the water of reaction can also be removed from the reacting mixture.

KGA has a lower solubility in said C4–C10-alcohols than in water. Removing the water during the esterification reaction according to the processes which are described in the prior art therefore generally leads to KGA deposits, since, with the reduction in water content in the esterification reaction, KGA precipitates out. To remove the solid deposits, processes must be regularly shut down and equipment cleaned. Downtimes and product losses occur.

The problem then underlying the present invention is that in the case of the processes described in the prior art for preparing ascorbic acid using C4- or higher alkyl esters as intermediates, solid deposits can regularly occur. This means that the yield, service life and operational reliability of the process are considerably impaired.

It is an object of the present invention to provide an advantageous process for preparing 2-keto-L-gulonic $C_4$–$C_{10}$-alkyl ester, without the disadvantages known from the prior art, for example relatively high alkyl ester consumption, low yield, long reaction times, discolorations and considerable byproduct content and which is, in particular, suitable for conversion to L-ascorbic acid.

We have found that this object is achieved by the embodiments described herein and characterized in the claims.

The invention therefore relates to a process for preparing 2-keto-L-gulonic $C_4$–$C_{10}$-alkyl ester by esterifying 2-keto-L-gulonic acid (KGA) with a $C_4$–$C_{10}$-alcohol, which comprises, in a preliminary esterification, reacting an aqueous KGA solution with a saturated, branched or unbranched $C_4$–$C_{10}$-alcohol under acid catalysis up to a degree of esterification of from 20% to 70%, preferably from 30% to 50%; and dehydrating the product in a continuous rectification apparatus using a $C_4$–$C_{10}$-alcohol, as a result of which the esterification reaction advances. The rectification apparatus can be a single-stage or multistage distillation apparatus as described extensively in the prior art. In particular, the rectification apparatus is to be constructed in such a manner that the esterification can be carried out according to the invention in the apparatus. Therefore, a rectification apparatus having high residence times of the solution on the plates, as described hereinafter, is advantageous.

For esterification, in principle, all $C_4$–$C_{10}$-alcohols are suitable, advantageously saturated, branched or unbranched alkyl alcohols having a carbon number greater than or equal to from 4 to 10 carbons, for example 1-butanol, 2-butanol, 2-methyl-1-propanol, 2-methyl-2-propanol, 1-pentanol, 2-pentanol, 3-pentanol, 1-hexanol, 2-hexanol, 1-heptanol, 2-heptanol, 1-octanol, 2-octanol, 3-octanol, 1-nonanol, 2-nonanol, 1-decanol, 2-decanol, 4-decanol, particularly preferably $C_4$–$C_8$-alcohols selected from the group consisting of 1-butanol, 2-butanol, 2-methyl-1-propanol, 2-methyl-2-propanol, 1-pentanol, 1-hexanol and 1-octanol. In a preferred embodiment, the alcohol used for esterification and dehydration is a $C_4$- to $C_6$-alcohol. A very particularly preferred alcohol is a $C_4$-alcohol, in particular n-butanol.

In the preliminary esterification, in a preferred embodiment, the alcohol is used in a mass ratio to the aqueous KGA solution of from 1:1 to 5:1, preferably from 2.5:1 to 3.5:1.

In a further embodiment, in the process, a homogeneous or heterogeneous acid catalyst is used for the acid catalysis. By using a catalyst, the reaction temperature can be kept low and thus the formation of thermal decomposition products can be avoided.

By adding an acid catalyst, the esterification reaction is catalyzed in the manner known per se.

Esterification catalysts which can be used are generally all homogeneous or heterogeneous acid catalysts which are known per se.

Suitable homogeneous catalysts are, for example, mineral acids or esters thereof. These include, in particular, phosphoric acid, phosphoric acid monobutyl ester, phosphoric acid dibutyl ester, phosphoric acid monopentyl ester, phosphoric acid dipentyl ester, sulfuric acid, sulfuric acid monobutyl ester, sulfuric acid monopentyl ester, hydrogen chloride, p-toluenesulfonic acid, methanesulfonic acid, trifluoromethanesulfonic acid, chlorosulfonic acid and trifluoroacetic acid. 2-Keto-L-gulonic acid or ascorbic acid can also be used as esterification catalysts.

Preferably, use is made of sulfuric acid, p-toluenesulfonic acid, methanesulfonic acid or monoalkyl sulfates of the alcohols used. The monoalkyl sulfates, at temperatures above 70° C., release sulfuric acid which then acts as a catalyst. Particularly preferred homogeneous acid catalysts are sulfuric acid and p-toluenesulfonic acid.

In the case of the abovementioned catalysts, these can either be added to one of the starting materials before the reaction or fed into the reactor as a separate stream.

Heterogeneous catalysts are advantageously fixed in the reactor in the hot reaction zone. For installing heterogeneous catalysts into distillation columns, numerous possible construction methods are described in the literature. These include delay trays, in which the catalyst can be disposed on the trays or in their downcomers, in addition, random packings, coiled and structured packings having worked-in catalyst.

Heterogeneous catalysts which can be used are the acid catalysts which are known per se, preferably acid ion exchangers and also zeolites.

The term "acid cation exchangers" is to be taken to mean commercially available resins or Detoxan, for example Lewatit® S 100, SP 112 or Lewatit® 2631 (Bayer) or Amberlite® 18 and IRA 120 or Amberlyst® 15 or Duolite® C 20, C 26 and C 264 (Rohm & Haas) or Dowex® ion exchangers.

Zeolites are crystalline aluminosilicates which have a highly ordered structure with a rigid three-dimensional network of $SiO_4$ or $AlO_4$ tetrahedra which are linked by shared oxygen atoms. The ratio of Si and Al atoms to oxygen is 1:2. The electrovalency of the aluminum-containing tetrahedra is compensated for by inclusion of cations into the crystal, for example of an alkali metal atom or hydrogen atom. Cation exchange is therefore possible. The spaces between the tetrahedral are occupied by water molecules before the dehydration by drying or calcining.

Suitable zeolites are, for example, those of the pentasil type, particularly aluminosilicate zeolites or borosilicate zeolites. By pre-coking, it is possible to adjust the activity of the catalysts for optimum selectivity of the desired reaction product.

Preferably, a mineral acid is used as catalyst, particularly preferably sulfuric acid.

The catalyst is used in amounts of from 0.02 to 0.03 mol, preferably in amounts of from 0.021 to 0.025 mol, for example 0.023 mol, per mole of 2-keto-L-gulonic acid.

In a further embodiment the reaction temperature of the entire esterification, that is to say during the preliminary esterification and the esterification in the reactive column, is from 50° C. to 120° C., preferably from 80° C. to 90° C.

Preferably, the preliminary esterification is carried out in a continuous process, for example in a continuous-flow stirred tank or other reactor.

The residence time in the reactor depends, inter alia, on the temperature and the degree of esterification to be achieved. In a preferred embodiment, a residence time of from 1 to 3 hours is selected, preferably 1.5 h, at a reaction temperature in the preliminary esterification of from 65° C. to 120° C., preferably from 80° C. to 90° C.

Preferably, the preliminary esterification in the inventive process is carried out at from 65° C. to 120° C., particularly preferably from 80° C. to 90° C. The choice of temperature depends on the desired reaction time and on the desired degree of esterification to be achieved and lies within the field of knowledge of an average person skilled in the art.

The invention therefore preferably relates to a process which is carried out under the following conditions:

mean residence time of the aqueous KGA in the stirred tank from 1 to 3 h, preferably from 1 to 1.5 h, at a reaction temperature from 65° C. to 120° C., preferably from 75° C. to 95° C., more preferably from 80° C. to 90° C.; at a mass ratio of KGA to $C_4$–$C_{10}$-alcohol of from 1:1 to 5:1, preferably from 2.5:1 to 3.5:1; and at reaction temperatures during the entire process from 50° C. to 120° C., preferably from 80° C. to 90° C., a degree of esterification of from 20 to 70% being achieved. Preferably, the conditions are chosen in such a manner that the degree of esterification is from 30% to 50%.

After the inventive preliminary esterification step, the product is fed according to the invention in a second step to a continuous rectification apparatus and further esterified there. The rectification apparatus is preferably a plate column, or a column having random or structured packing. The inventive preliminary esterification described herein avoids loss of KGA occurring through solid deposits in the apparatus on the internals such as plates, random packings or structured packings. The solution fed to the apparatus already has a high proportion of KGA ester and thus a higher solubility for KGA.

In one embodiment, therefore, in the inventive process, the continuous rectification apparatus (2) is equipped with an evaporator (3) and a condenser (4), and in a particularly preferred embodiment, in addition with a phase-separation apparatus (5), and preferably a vacuum system (6).

In a further embodiment, the first rectification apparatus is supplemented by a second rectification apparatus at the preliminary esterification apparatus. Therefore, in one embodiment, the preliminary esterification reactor (1) is equipped with an additional column (7), an additional evaporator (8), possibly an additional condenser (9) and possibly an additional phase-separation apparatus (10).

Rectification columns are extensively described in the prior art, for example in Thermische Trennverfahren [Thermal separation processes], K. Sattler, VCH Verlagsgesellschaft, Weinheim, 1995, in particular chapter 2 and chapter 7, or in DE 199 38 980, the contents of which are expressly incorporated herein by reference.

Preferably, rectification columns are used which are particularly suitable for carrying out the inventive esterification reaction. These columns are distinguished by a high residence time of the reaction solution in the respective stage. Thus, advantageously, for example, columns can be used which have a high liquid holdup, for example highly dammed plates of a plate column. Therefore, suitable columns for the inventive process are, in particular, also columns which have only a few separation stages, provided that a suitable residence time is ensured. Particularly advantageously, in particular a low temperature is used, for example below 100° C., preferably from 80° C. to 90° C.

The inventive embodiment leads to a product having low amounts of byproduct and good color numbers.

In one embodiment the preliminary esterification is carried out without removing water, but, in the preliminary esterification, water can also be distilled off during the reaction by using a second rectification column, if the KGA precipitated out in the reaction solution is redissolved during the esterification.

Advantageously, in the inventive process, the aqueous KGA solution can be concentrated before entry into the preliminary esterification reaction up to the solubility limit of KGA or beyond. The solubility limit of KGA is a function of the temperature of the solution and the elevated ester content. Preferably, the KGA solution is concentrated to a KGA mass fraction up to the solubility limit at from 30° C. to 70° C., more preferably from 40° C. to 60° C., most preferably at from 45° C. to 55° C. At a temperature of 50° C., for example, the solubility limit is reached at a KGA mass fraction of 50%.

If the aqueous KGA solution is concentrated before the esterification to above the solubility limit, a suspension is formed. This suspension can then be esterified according to the invention, in which case suitable reaction apparatuses according to the knowledge of those skilled in the art are to be used, for example a preliminary esterification reaction as described in the examples. Owing to the advancing preliminary esterification and the elevated ester content in the solution, the precipitated KGA redissolves. In this case also, solids deposition in the following rectification column does not occur. Rather, the inventive process can be operated particularly economically in this manner, since the input into the esterification reaction can have a higher KGA concentration than is possible in the processes described in the prior art. This leads to savings, in particular in energy. The takeoff into the distillation column is performed in such a manner that no solid is carried over, for example from the upper region of the preliminary esterification reactor just below the liquid surface.

In a further embodiment, the present inventive process is part of a process for preparing ascorbic acid, the 2-keto-L-gulonic acid $C_4$–$C_{10}$-alkyl ester prepared being converted in one or more steps to L-ascorbic acid, for example by means of base- or acid-catalyzed lactonization.

Particularly preferably, the inventive process therefore comprises the following steps:
 a) preparing an aqueous KGA solution, for example from a fermentation broth;
 b) concentrating the aqueous KGA solution at from 30° C. to 60° C., advantageously 50° C.;
 c) preliminarily esterifying the KGA solution with a $C_4$–$C_{10}$-alkyl alcohol, preferably butanol, using the process described above;
 d) removing the water with a $C_4$- to $C_{10}$-alkyl alcohol in a rectification apparatus using the process described above;
 e) concentrating the prepared KGA ester; if appropriate transesterifying the KGA $C_4$–$C_{10}$-alkyl alcohol ester using a $C_1$–$C_3$-alkyl alcohol, in particular methanol;
 f) lactonizing the ester to give L-ascorbic acid; and
 g) isolating the free L-ascorbic acid;

where each of these steps except for (c) and (d) is optional or can be accompanied by further intermediate stages as are described in the prior art, for example evaporating and concentrating the solutions, filtration, for example microfiltration or ultrafiltration, precipitation, crystallization, extraction, liberation of acids from salts. Preferably, the inventive process in one embodiment comprises all said steps (a) to (g).

A suitable KGA solution can result, for example, via the workup of a fermentation broth of KGA-producing microorganisms.

A fermentation solution can be worked up using the processes described in the prior art, for example via filtration or isolation of Na-KGA by crystallization or precipitation.

A solution, in particular the KGA solution, can be concentrated by processes known in the prior art, for example by evaporation or by osmosis, for example by reverse osmosis. Preferably, operations are carried out under mild conditions, in particular at temperatures of from 40° C. to 60° C., and at reduced pressure.

The lactonization can proceed under acid or base catalysis. Appropriate processes are extensively described in the prior art.

The publications set forth herein are expressly incorporated by reference.

The invention is illustrated with reference to the following figures:

FIG. 1 shows the inventive process without water takeoff in the preliminary esterification using a rectification apparatus: preliminary esterification reactor (1) having a following rectification apparatus (2) having an evaporator (3), a condenser (4), a phase-separation apparatus (5) and a vacuum system (6).

Figure 2:
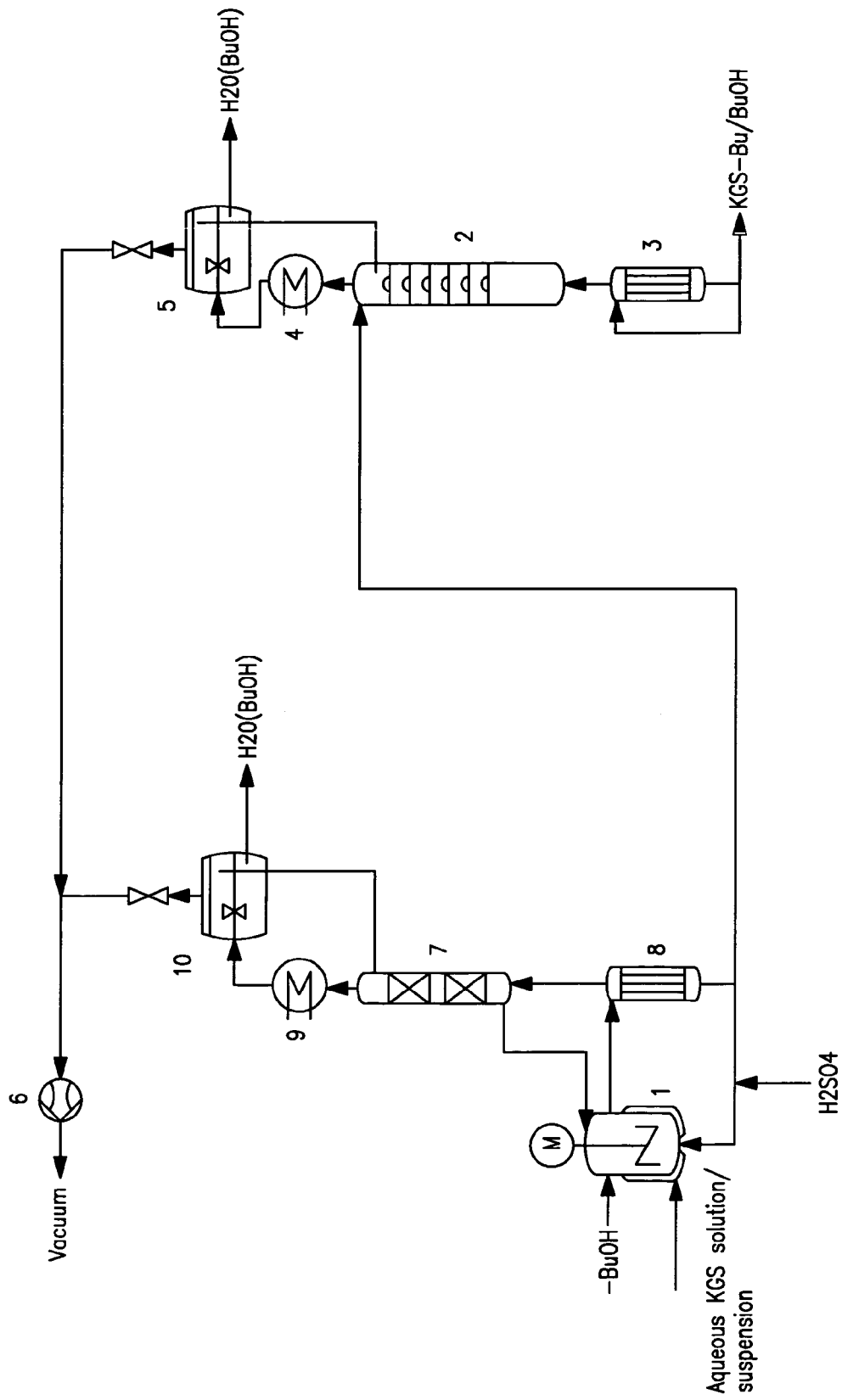

FIG. 2 shows the inventive process with water takeoff in the preliminary esterification having a second rectification apparatus: preliminary esterification reactor (1) having following rectification apparatus (3) having an evaporator (2), a condenser (4), a phase-separation apparatus (5) and a vacuum system (6), where the preliminary esterification reactor (1) is equipped with an additional rectification apparatus (7), an additional evaporator (8), an additional condenser (9) and an additional phase-separation apparatus (10).

The present invention is illustrated by the following examples without this being considered as limiting.

EXAMPLE 1

A general embodiment of the inventive process is shown in FIG. 1: an aqueous KGA solution which is concentrated at 50° C. to the solubility limit (50% KGA mass fraction) is mixed with n-butanol, in a mass ratio of from 1:1 to 3:1, preferably from 1.5:1 to 2:1, and with catalytic amounts of concentrated sulfuric acid and fed to a wall-heated, continuous-flow stirred tank or other reactor (1), the volume of which is such that the residence time is from 1 to 3 h, preferably 1.5 h. The heater of reactor 1 is set so that from 65 to 120° C., preferably from 80 to 90° C., are established in the interior of the reactor. In the reactor 1 a degree of esterification of from 30 to 60% is thus achieved. The mixture exiting from 1 is fed to a multistage rectification apparatus (2), for example a plate column or packed column. The continuous rectification apparatus (2) is equipped with an evaporator (3), a condenser (4) and a phase-separation apparatus (5), and also a vacuum system (6). The influent mixture runs downward in the apparatus (1) under the influence of gravity, while the predominantly n-BuOH-containing vapors from the evaporator (3) flow in the opposite direction to the liquid. The concentration of water in the liquid decreases on the path downward, from separation stage to separation stage, as a result of which the esterification reaction advances (reactive distillation). At the top of the apparatus 2, the vapors of azeotropic composition are condensed and are mechanically separated into a predominantly BuOH-containing phase and a predominantly aqueous phase. The aqueous phase is taken off and fed to wastewater treatment, if appropriate with BuOH recovery, and the BuOH phase is recirculated as reflux back to the rectification apparatus 1. The temperature in the evaporator 3 is set to from 65 to 110° C., preferably from 80 to 90° C., by applying a suitable vacuum (6). At the bottom of the evaporator 3 a virtually anhydrous mixture of KGA butyl ester and BuOH is taken off. As a result of the inventive preliminary reactor, usually no solids precipitation occurs in the rectification apparatus 2.

EXAMPLE 2

FIG. 2 shows a further embodiment of the inventive process: here the preliminary esterification reactor 1 is equipped with an additional column 2, an additional evaporator 3, an additional condenser 4 and an additional phase-separation apparatus 5 and thus as soon as in the preliminary esterification a partial removal of water and thus a higher degree of esterification are achieved. Since the preliminary esterification proceeds further in the stirred tank (KGA is a high-boiler), the internals of the column 2 cannot be coated with solid.

EXAMPLE 3

An aqueous KGA solution was concentrated by multistage water evaporation (for example in falling-film evaporators), in the last stage at approximately 50° C. and appropriate vacuum, to a concentration of 50% KGA (m/m), so that no solid precipitates out. This solution was mixed with n-butanol (n-BuOH), in a heated stirred tank, for example, in a mass ratio of 1.73:1, then a small amount of sulfuric acid ($H_2SO_4$) is added as catalyst (approximately 1% mass fraction based on KGA). The clear solids-free mixture was esterified at 85° C. for from 1 to 1.5 h. Despite this relatively high mass fraction of water in the mixture of approximately 18%, a KGA conversion to KGA butyl ester of from 45 to 50% was achieved. In the further esterification of the mixture in a reactive distillation (for example according to DE 199 38 980), no solids precipitation occurs.

EXAMPLE 4

In a stirred tank which is externally heated via a oil bath (max. capacity 100 $cm^3$), 23 g of dry, calcined KGA were dissolved completely in 23 g of water at 85° C. within a few minutes. Then, 80 g of n-butanol preheated to 85° C., and also 0.3 g of concentrated sulfuric acid (96%) were added and the mixture was stirred for 1.5 h under reflux. The KGA dissolved completely. Then, the mass fraction of KGA butyl ester in the mixture was determined using HPLC; a mass fraction of 10.68% was measured. This corresponds to a degree of ester formation of 45.5%.

EXAMPLE 5

The apparatus was then extended by a water-cooled condenser and a vacuum pump. In a second experiment carried out identically except for the above-described point, 75 g of the liquid were distilled off in the course of 30 min at 85° C. close to the boiling point by applying a vacuum, without sampling. The liquid mixture in the stirred tank remained clear to the end, and no solids precipitation was observed. Determination of the residual water content by the Karl Fischer method gave a residual water content of 0.4% (m/m).

EXAMPLE 6

In a further experiment, as in the second experiment, 23 g of dry, calcined KGA were completely dissolved in 23 g of water at 85° C. in the course of a few minutes. Then 80 g of n-butanol preheated to 85° C. and 0.3 g of concentrated sulfuric acid (96%) were added and distillation was begun immediately by applying the vacuum. Cloudiness occurred in the interim due to solids precipitation. The solids redissolved as the distillation proceeded further.

We claim:

1. A process for preparing 2-keto-L-gulonic $C_4$–$C_{10}$-alkyl esters by esterifying 2-keto-L-gulonic acid (KGA) with a saturated, branched or unbranched $C_4$–$C_{10}$-alcohol, which comprises, in a preliminary esterification, reacting an aqueous KGA solution with a $C_4$–$C_{10}$-alcohol under acid catalysis up to a degree of esterification of from 20% to 70% and dehydrating the product in a continuous rectification apparatus using a $C_4$–$C_{10}$-alcohol, as a result of which the esterification reaction advances.

2. A process as claimed in claim 1, wherein the alcohol is a saturated, branched or unbranched alkyl alcohol having from 4 to 10 carbons.

3. A process as claimed in claim 1, wherein, in the preliminary esterification, the alcohol is used in a mass ratio to the KGA content in the aqueous solution of from 1:1 to 5:1.

4. A process as claimed in claim 1, wherein the catalyst is an acid heterogeneous or homogeneous catalyst.

5. A process as claimed in claim 1, wherein the catalyst is a mineral acid.

6. A process as claimed in claim 1, wherein the preliminary esterification is carried out in a continuous-flow stirred tank.

7. A process as claimed in claim 1, which is carried out under the following conditions:
   a) mean residence time of the aqueous KGA in the preliminary esterification from 1 to 3 h,
   b) reaction temperature in the preliminary esterification from 65° C. to 120° C.; and/or
   c) mass ratio of KGA content to $C_4$–$C_{10}$-alcohol from 1:1 to 5:1; and/or
   d) reaction temperatures during the entire process from 50° C. to 120° C. and/or
   e) use of from 0.02 to 0.03 mole of sulfuric acid per mole of KGA as catalyst.

8. A process as claimed in claim 1, wherein the aqueous KGA solution, before entry into the preliminary esterification reactor, is concentrated up to the solubility limit of KGA.

9. A process as claimed in claim 1, wherein the aqueous KGA solution, before entry into the preliminary esterification reactor, is concentrated to above the solubility limit of KGA.

10. A process as claimed in claim 1, wherein the continuous rectification apparatus is equipped with an evaporator and a condenser.

11. A process as claimed in claim 1, wherein the preliminary esterification reactor is equipped with an additional column, an additional evaporator and an additional condenser.

12. A process for preparing ascorbic acid, which comprises the process of claim 1 followed by converting the 2-keto-L-gulonic $C_4$–$C_{10}$-alkyl ester prepared to L-ascorbic acid in one or more steps.

13. A process as claimed in claim 2, wherein the $C_4$–$C_{10}$-alcohol is n-butanol.

14. A process as claimed in claim 10, wherein the continuous rectification apparatus is further equipped with a phase-separation apparatus and/or a vacuum system.

15. A process as claimed in claim 11, wherein the preliminary esterification reactor is further equipped with an additional phase-separation apparatus.

* * * * *

UNITED STATES PATENT AND TRADEMARK OFFICE
CERTIFICATE OF CORRECTION

PATENT NO. : 7,091,375 B2
APPLICATION NO. : 10/534334
DATED : August 15, 2006
INVENTOR(S) : Thomas Domschke et al.

It is certified that error appears in the above-identified patent and that said Letters Patent is hereby corrected as shown below:

On Title Page

Item (54), "METHOD FOR THE PRODUCTION OF 2=-KETO-L-GULONIC ACID $C_4C_{10}$ ALKYL ESTERS" should read -- PROCESS FOR PREPARING 2-KETO-L-GULONIC $C_4$-$C_{10}$-ALKYL ESTERS --

On Title Page Item (75), Inventors, "Thomas Domschke, Speyer (DE); Martin Merger, Ludwigshafen (DE); Georg Grossman, Mannheim (DE); Tillmann Faust, Weisenheim (DE)" should read -- Thomas Domschke, Speyer (DE); Martin Merger, Frankenthal (DE); Georg Grossman, Mannheim (DE); Tillmann Faust, Weisenheim (DE) --

On Title Page Item (56), References Cited, FOREIGN PATENT DOCUMENTS

"DE    198 29 809    1/1999

DE    199 38 980    2/2001

DE    199 54 511    5/2001

EP    0 403 351    12/1990" should read

-- DE    198 298 09    1/1999

DE    199 38 980    2/2001

DE    199 54 511    5/2001

EP    0 403 351    12/1990

UNITED STATES PATENT AND TRADEMARK OFFICE
CERTIFICATE OF CORRECTION

PATENT NO. : 7,091,375 B2
APPLICATION NO. : 10/534334
DATED : August 15, 2006
INVENTOR(S) : Thomas Domschke et al.

It is certified that error appears in the above-identified patent and that said Letters Patent is hereby corrected as shown below:

On Title Page, Item (56) (cont'd)

| | | |
|---|---|---|
| EP | 0 403 993 | 12/1990 |
| EP | 0 535 927 | 4/1993 |
| EP | 0 671 405 | 9/1995 |
| WO | WO-97/43433 | 11/1997 |
| WO | WO-99/03853 | 1/1999 |
| WO | WO-01/85711 | 11/2001 -- |

Signed and Sealed this

Ninth Day of January, 2007

JON W. DUDAS
*Director of the United States Patent and Trademark Office*